United States Patent
Anikhindi et al.

(10) Patent No.: US 7,988,771 B2
(45) Date of Patent: Aug. 2, 2011

(54) APPARATUS AND METHOD FOR CONTROLLING ODOR WITHIN AN APPLIANCE

(75) Inventors: Sanjay Manohar Anikhindi, Karnataka (IN); Mark Wilson, Simpsonville, KY (US); Sheena Ritchie, Louisville, KY (US)

(73) Assignee: General Electric Company, Schenectady, NY (US)

( * ) Notice: Subject to any disclaimer, the term of this patent is extended or adjusted under 35 U.S.C. 154(b) by 720 days.

(21) Appl. No.: 11/437,900

(22) Filed: May 19, 2006

(65) Prior Publication Data

US 2007/0266725 A1 Nov. 22, 2007

(51) Int. Cl.
*B01D 53/02* (2006.01)

(52) U.S. Cl. ........... 96/108; 96/19; 96/112; 95/8; 95/14; 62/78; 62/317

(58) Field of Classification Search .............. 62/78, 317; 96/19, 108, 112; 95/8, 14
See application file for complete search history.

(56) References Cited

U.S. PATENT DOCUMENTS

| | | | |
|---|---|---|---|
| 4,948,567 A * | 8/1990 | Atarashiya | 422/122 |
| 5,078,971 A | 1/1992 | Matuda et al. | |
| 5,230,220 A * | 7/1993 | Kang et al. | 62/78 |
| 5,291,742 A | 3/1994 | Kawatani et al. | |
| 5,347,820 A * | 9/1994 | In Gweon | 62/78 |
| 5,501,084 A * | 3/1996 | Chang et al. | 62/264 |
| 5,568,730 A | 10/1996 | Kim et al. | |
| 5,924,292 A | 7/1999 | Markum | |
| 5,948,355 A * | 9/1999 | Fujishima et al. | 422/4 |
| 6,286,330 B1 | 9/2001 | Kopf | |
| 6,370,703 B1 * | 4/2002 | Kim et al. | 4/216 |
| 6,447,731 B1 * | 9/2002 | Sun et al. | 422/121 |
| 6,454,841 B1 | 9/2002 | Kaiser | |
| 6,918,259 B2 | 7/2005 | Anderson et al. | |
| 2002/0152969 A1* | 10/2002 | Grigsby et al. | 119/500 |
| 2004/0007000 A1* | 1/2004 | Takeda et al. | 62/78 |
| 2005/0022549 A1 | 2/2005 | Anderson et al. | |
| 2005/0224069 A1* | 10/2005 | Patil et al. | 126/299 D |

* cited by examiner

*Primary Examiner* — Robert J Hill, Jr.
*Assistant Examiner* — Christopher P Jones
(74) *Attorney, Agent, or Firm* — Armstrong Teasdale LLP

(57) ABSTRACT

An apparatus for controlling odor within a refrigeration appliance is provided. The apparatus includes a frame removably positioned within an airflow path configured to supply cooled air to a food storage compartment of the refrigeration appliance. The frame defines a chamber. A filter medium is positioned within the chamber. The filter medium is configured to filter air channeled therethrough and remove odorous molecules.

17 Claims, 9 Drawing Sheets

APPARATUS AND METHOD FOR CONTROLLING ODOR WITHIN AN APPLIANCE

BACKGROUND OF THE INVENTION

This invention relates generally to appliances and, more particularly, to apparatus and methods for controlling odors within appliances.

Certain food products, such as fish, strawberries, onions and garlic, emit odors. When such food products are stored within an appliance, such as within a fresh food storage compartment or a freezer storage compartment of a refrigerator, the odor emissions lead to undesirable characteristic smells within the appliance. As the consumer opens the refrigerator door, for example, the consumer may smell such undesirable odors. Additionally, these odors released by such food products may contaminate other generally non-odorous food products, such as milk, water or ice. As a result, the contaminated food products may smell differently than originally perceived. Conventional methods for preventing such odors from contaminating other food products include sealing or packing the food products. However, it is not feasible to seal or package all food products and, in many cases, sealed or packaged food products may still emit undesirable odors.

BRIEF DESCRIPTION OF THE INVENTION

In one aspect, an apparatus for controlling odor within a refrigeration appliance is provided. The apparatus includes a frame removably positioned within an airflow path configured to supply cooled air to a food storage compartment of the refrigeration appliance. The frame defines a chamber. A filter medium is positioned within the chamber. The filter medium is configured to filter air channeled therethrough and remove odorous molecules.

In another aspect, a refrigeration appliance is provided. The refrigeration appliance includes a food storage compartment. An air supply duct extends into the food storage compartment. The air supply duct defines an airflow path configured to supply cooled air to the food storage compartment. A vapor compression cycle system includes an evaporator. The vapor compression cycle system is charged with a refrigerant and configured to transfer heat from air within the airflow path to the refrigerant as the air passes over the evaporator. An odor control assembly includes a frame removably positioned within an opening formed in the air supply duct. The frame defines a chamber extending into at least a portion of the airflow path and a filter medium positioned within the frame. The filter medium is configured to filter air channeled therethrough and remove odorous molecules.

In another aspect, a method for removing an odor from within a food storage compartment of an appliance is provided. The method includes positioning an odor control assembly within an airflow path defined within the food storage compartment. The airflow path is configured to supply cooled air to the food storage compartment. The odor control assembly includes a frame removably positioned within the airflow path. The frame defines a chamber. A filter medium is positioned within the chamber. The filter medium is configured to filter air channeled therethrough and remove odorous molecules. At least a portion of the cooled air is channeled through the odor control assembly defined within the frame and the odorous molecules are removed from the channeled air.

DETAILED DESCRIPTION OF THE INVENTION

The present invention provides an apparatus and method for controlling and/or removing odors within an appliance, such as a refrigeration appliance, to reduce the odor level to a significantly lower level as perceived by a human's sense of smell. In one embodiment, an apparatus and method is provided for reducing odor within a refrigerator storage compartment, wherein an odor level is sensed to enable active control of the odor level and provide feedback to the consumer.

The present invention is described below in reference to its application in connection with and operation of a household refrigerator. However, it will be apparent to those skilled in the art and guided by the teachings herein provided that the present invention is likewise applicable to any appliance including, without limitation, industrial refrigerators and refrigeration systems, freezers and any suitable industrial or household appliance.

Figure 1:
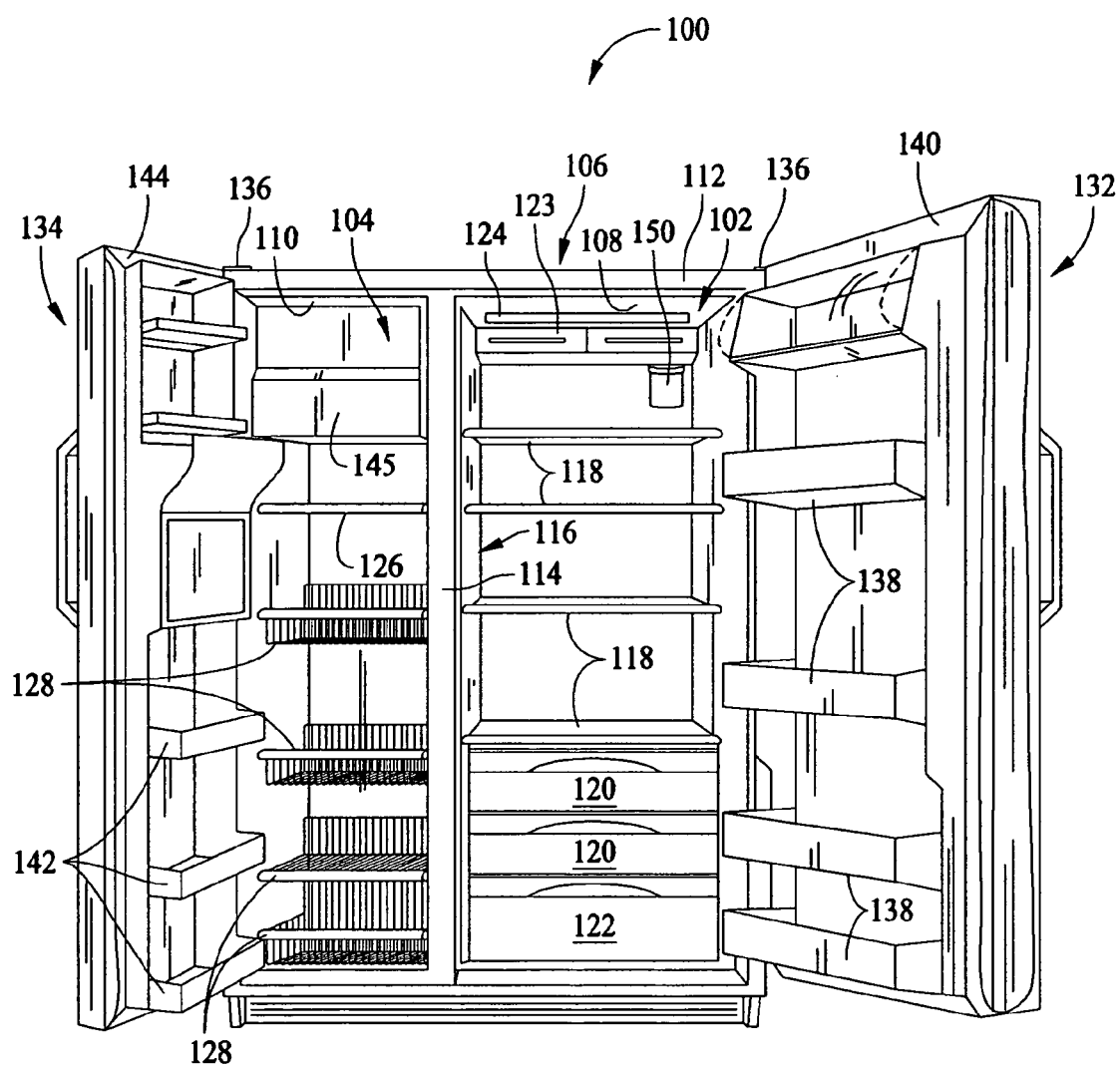
FIG. 1 is a perspective view of an exemplary refrigerator.

FIG. 1 is a perspective view of an exemplary refrigerator 100 in which exemplary embodiments of the present invention may be practiced and for which the benefits of the present invention may be realized. It is apparent to those skilled in the art and guided by the teachings herein provided that the apparatus and/or method, as described herein, may likewise be practiced in any suitable refrigerator or appliance. Therefore, refrigerator 100 as described and illustrated herein is for illustrative purposes only and is not intended to limit the herein described apparatus and/or method in any aspect.

FIG. 1 illustrates a side-by-side refrigerator 100 including a fresh food storage compartment 102 and a freezer storage compartment 104. Fresh food storage compartment 102 and freezer storage compartment 104 are arranged side-by-side. In one embodiment, refrigerator 100 is a commercially available refrigerator from General Electric Company, Appliance Park, Louisville, Ky. 40225, and is modified to incorporate the herein described apparatus. In an alternative embodiment, refrigerator 100 is a top and bottom mount refrigerator.

Fresh food storage compartment 102 and freezer storage compartment 104 are contained within an outer case 106 having inner liners 108 and 110. A space between outer case 106 and inner liners 108 and 110, and between inner liners 108 and 110, is filled with foamed-in-place insulation. In one embodiment, outer case 106 is formed by folding a sheet of a suitable material, such as pre-painted steel, into an inverted U-shape to form a top wall and side walls of outer case 106. In this embodiment, outer case 106 is formed separately and coupled to the side walls and a bottom frame that provides support for refrigerator 100. Inner liners 108 and 110 are molded from a suitable plastic material to form fresh food storage compartment 102 and freezer storage compartment 104, respectively. In an alternative embodiment, inner liners 108 and/or 110 are formed by bending and welding a sheet of a suitable metal, such as steel. The illustrative embodiment includes two separate inner liners 108 and 110, as refrigerator 100 is a relatively large capacity unit and separate liners add strength and are easier to maintain within manufacturing tolerances. In smaller refrigerators, a single liner is formed and a mullion spans between opposite sides of the liner to divide it into a freezer storage compartment and a fresh food storage compartment.

A breaker strip 112 extends between a case front flange and outer front edges of inner liners 108 and 110. Breaker strip 112 is formed from a suitable resilient material, such as an extruded acrylo-butadiene-styrene based material (commonly referred to as ABS).

The insulation in the space between inner liners 108 and 110 is covered by another strip of suitable resilient material, commonly referred to as a mullion 114. In this embodiment, mullion 114 is formed of an extruded ABS material. Breaker strip 112 and mullion 114 form a front face, and extend completely around inner peripheral edges of outer case 106 and vertically between inner liners 108 and 110. Mullion 114, the insulation between compartments, and a spaced wall of liners separating the compartments, may be collectively referred to herein as a center mullion wall 116.

Shelves 118 and slide-out drawers 120 normally are provided in fresh food storage compartment 102 to support items being stored therein. In one embodiment, a refrigerator control system including a controller 123 selectively controls refrigerator operation and/or features according to user preference via manipulation of a control interface 124 mounted in an upper region of fresh food storage compartment 102 and coupled to controller 123. At least one shelf 126 and/or at least one wire basket 128 are also provided in freezer storage compartment 104.

Controller 123 is mounted within refrigerator 100 and is programmed to perform functions described herein. As used herein, the term "controller" is not limited to integrated circuits referred to in the art as a microprocessor, but broadly refers to computers, processors, microcontrollers, microcomputers, programmable logic controllers, application specific integrated circuits and/or other programmable circuits, and these terms are used interchangeably herein.

Figure 2:
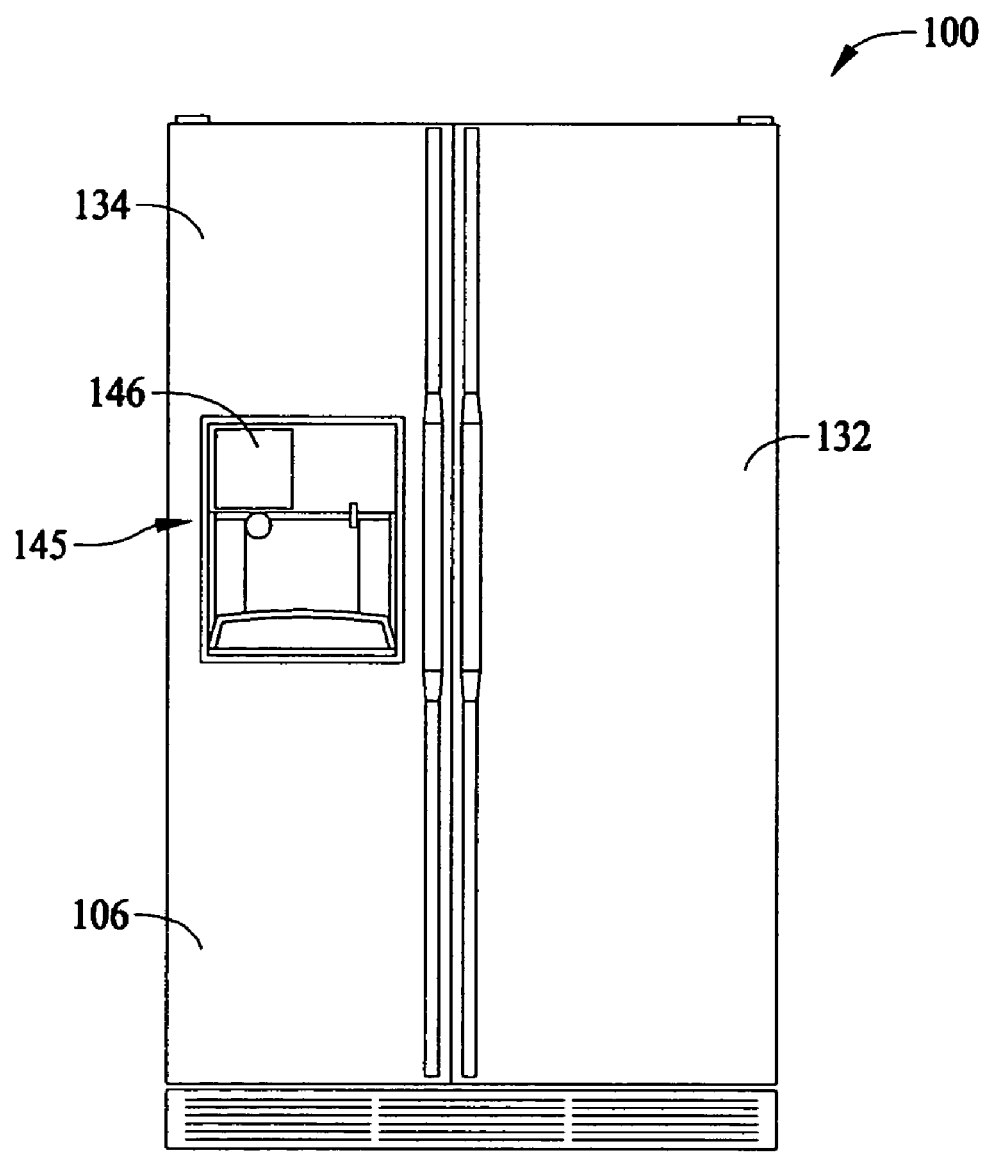
FIG. 2 is a front view of the refrigerator shown in FIG. 1.

A fresh food door 132 and a freezer door 134 close openings providing access to fresh food storage compartment 102 and freezer storage compartment 104, respectively. Each door 132, 134 is mounted by a top hinge 136 and a cooperating bottom hinge (not shown) to rotate about an outer vertical edge between an open position, as shown in FIG. 1, and a closed position, as shown in FIG. 2. In one embodiment, fresh food door 132 includes a plurality of storage shelves 138 and a sealing gasket 140. Similarly, freezer door 134 includes a plurality of storage shelves 142 and a sealing gasket 144.

In one embodiment, freezer storage compartment 104 includes an automatic ice maker 145 including a dispenser 146 provided in freezer door 134 so that ice can be dispensed without opening freezer door 134. In one embodiment, ice maker 145 includes a number of electromechanical elements that manipulate a mold to shape ice as it freezes, a mechanism to remove or release frozen ice from the mold and a primary ice bucket for storage of ice produced in the mold. Periodically, the ice supply is replenished by ice maker 145 as ice is removed from the primary ice bucket. The storage capacity of the primary ice bucket is generally sufficient for normal use of refrigerator 100. In a particular embodiment, dispenser 146 is also configured to dispense chilled water, as desired by the consumer, through freezer door 134.

Refrigerator 100 includes a machinery compartment (not shown) that at least partially contains components of a vapor compression cycle system 147 for executing a known vapor compression cycle for cooling air. The components include a compressor, a condenser, an expansion device, and an evaporator 148 (shown schematically in FIG. 5) coupled in series and charged with a refrigerant. Evaporator 148 is a type of heat exchanger that transfers heat from air passing over evaporator 148 to a refrigerant flowing through evaporator 148, thereby causing the refrigerant to vaporize. The cooled air is used to refrigerate one or more refrigerator or freezer storage compartments via fans (not shown). Collectively, the vapor compression cycle components in a refrigeration circuit, associated fans and associated compartments are referred to herein as a "sealed system." The construction of the sealed system is well known and therefore not described in detail herein. The sealed system is operable to force cold air through the refrigerator.

Figure 3:
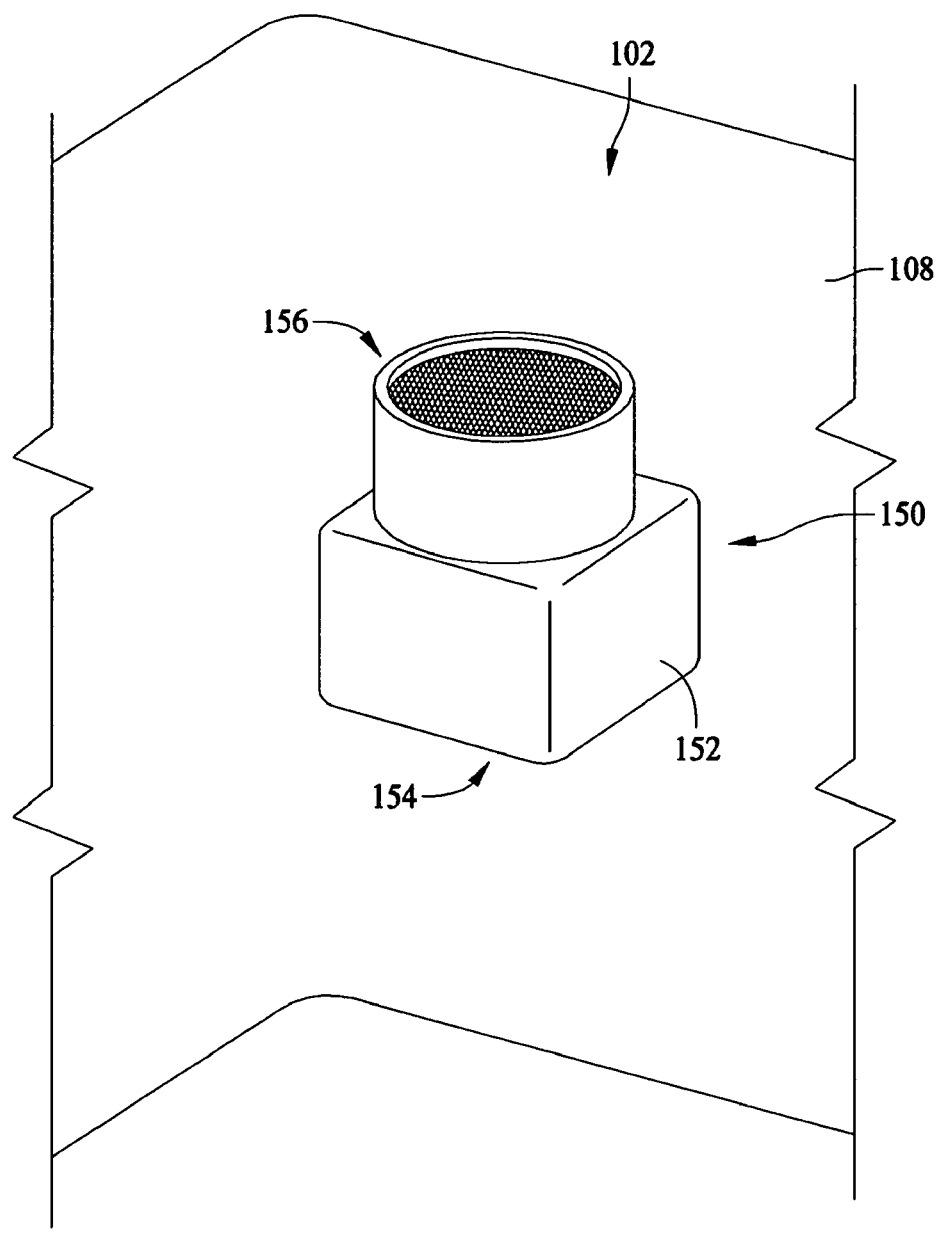
FIG. 3 is a perspective view of an exemplary odor control assembly suitable for incorporation into the refrigerator shown in FIG. 1.
Figure 4:
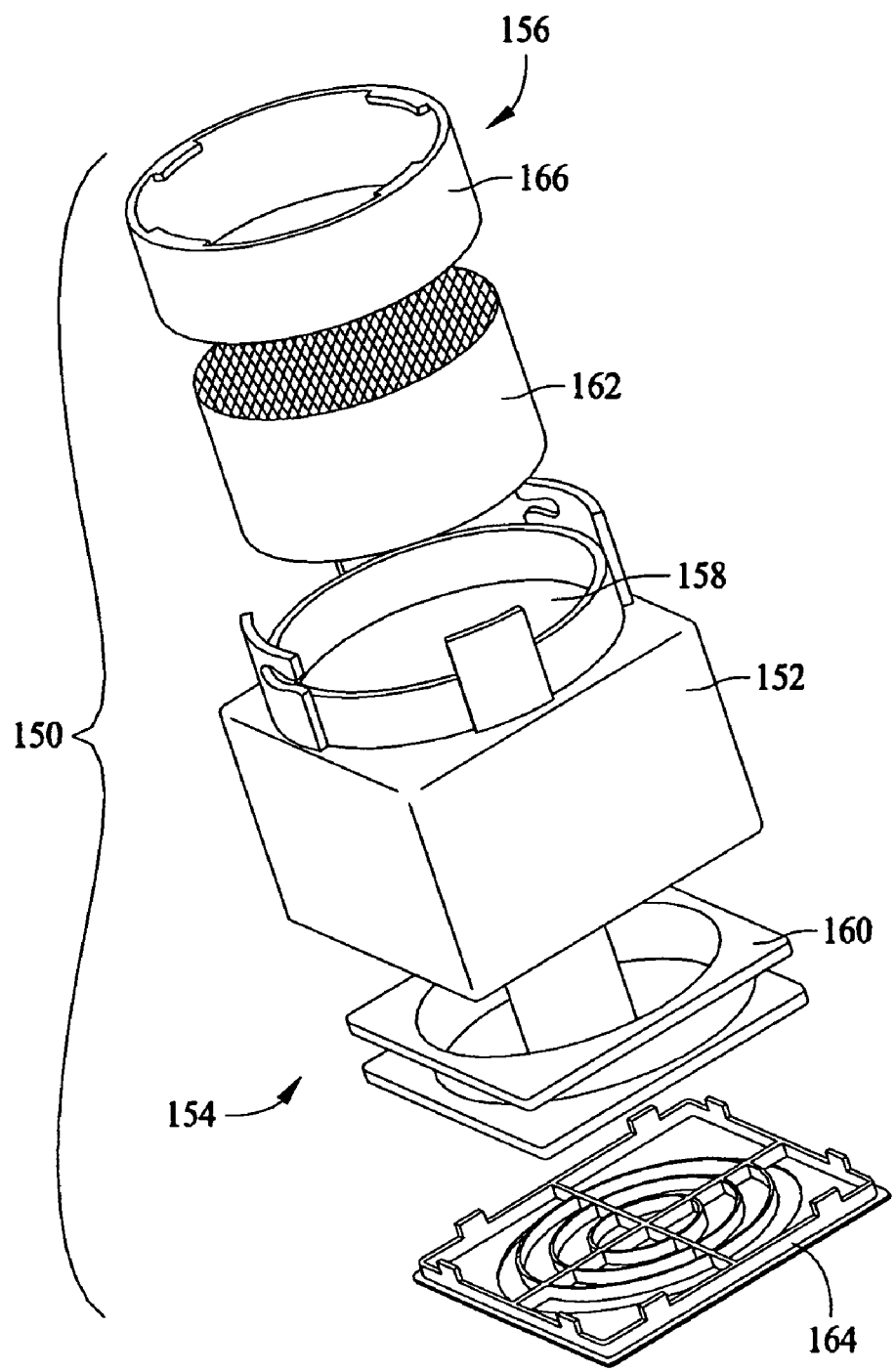
FIG. 4 is an exploded perspective view of the odor control assembly shown in FIG. 3.

Referring further to FIGS. 3 and 4, in one embodiment refrigerator 100 includes an odor control assembly 150 mounted at a suitable location within fresh food storage compartment 102 and configured to regulate and/or control a level of odor emitted from the food products stored within fresh food storage compartment 102. In alternative embodiments, odor control assembly 150 is mounted with respect to any suitable location within freezer storage compartment 104. In one embodiment, odor control assembly 150 is a dedicated system that operates independently from the refrigerator control system for facilitating efficient and effective odor control and design flexibility.

In one embodiment, odor control assembly 150 is positioned within an airflow path at an outlet of fresh food storage compartment 102, where the odor is absorbed by the air due to the relatively higher temperature of the air. By positioning odor control assembly 150 at the airflow outlet of fresh food storage compartment 102, the odor is prevented from reaching colder parts of refrigerator 100, where the odor may condense.

As shown in FIG. 3, odor control assembly 150 includes a frame 152. In one embodiment, frame 152 is coupled to inner liner 108 of refrigerator 100. Frame 152 forms a first end 154 and an opposing second end 156. Frame 152 further defines a chamber 158 that extends between first end 154 and second end 156. Referring further to FIG. 4, a fan 160 is positioned with respect to first end 154. In one embodiment, fan 160 includes a DC brushless fan that is coupled to first end 154. Fan 160 is configured for facilitating channeling air through chamber 158. In this embodiment, fan 160 facilitates air flow through odor control assembly 150 such that air containing odor molecules is channeled through chamber 158 from first end 154 to second end 156. A filter medium 162 is positioned within chamber 158. Filter medium 162 is configured to filter air channeled through chamber 158 and absorb odorous molecules. Filter medium 162 has a suitable pressure drop across a thickness of filter medium 162 such that the odor removal efficiency is not compromised. As a result, in an alternative embodiment, the refrigerator air moving device is utilized without a need for additional fans to operate odor control assembly 150. In a further alternative embodiment, filter medium 162 includes a suitable amount of material for facilitating predictably adjusting a useful life of filter medium 162 such that replacement of filter medium 162 can be synchronized with other refrigerator maintenance, such as replacement of a water filter every six months, for example.

As shown in FIG. 4, a grill 164 is coupled with respect to fan 160 for facilitating preventing a consumer and/or food products from undesirably contacting and/or interfering with fan 160 during operation. Further, a cap 166 is removably coupled to frame 152 to retain filter medium 162 properly positioned within chamber 158. In one embodiment, cap 166 is rotatably coupled to frame 152. Cap 166 is removable in order to remove filter medium 162 from within chamber 158 for facilitating cleaning filter medium 162 or replacing filter medium 162 with a new filter medium.

In one embodiment, filter medium 162 includes an adsorptive grid or mesh structure including activated carbon. The adsorptive grid structure has a relatively large porosity and forms a suitable surface area for adsorbing the odorous molecules on the surface and/or within cavities formed by the grid structure. In a particular embodiment, filter medium 162 is made of a carbon material without any carrier for shaping and/or holding the carbon material. Filter medium 162 continues to adsorb odor until filter medium 162 is saturated with odor molecules. Upon saturation, filter medium 162 is removed from within chamber 158 and cleaned or replaced with a new filter medium 162. In one embodiment, filter medium 162 includes a catalyst material dispersed throughout filter medium 162 for facilitating improving the odor removal efficiency of filter medium 162 and/or replenishing filter medium 162 to extend a useful life of filter medium 162. In this embodiment, the catalyst material contacts the odor molecules held within filter medium 162. The catalyst material facilitates a reaction between the odor molecules and the surrounding air and/or moisture to create by-products that are generally non-odorous. In a particular embodiment, filter medium 162 includes an activated carbon material with a low temperature catalyst, such as manganese dioxide ($MnO_2$), dispersed within filter medium 162 to improve the useful life of filter medium 162 by replenishing the activated carbon.

In an alternative embodiment, filter medium 162 includes a photocatalyst material, such as titanium dioxide ($TiO_2$), which is coated on at least an outer surface of filter medium 162. In this alternative embodiment, the outer surface of filter medium 162 is irradiated with an ultraviolet light having a wavelength of about 360 nm. The photocatalyst is energized with the ultraviolet light for facilitating a reaction between the odor molecules, oxygen and/or moisture in the surrounding air. In a particular embodiment, surfaces within fresh food storage compartment 102 which contact odorous food products are coated with the filtering material. Transparent surfaces, such as surfaces of shelves and/or pans placed within fresh food storage compartment, are coated with a $TiO_2$ material. The ultraviolet light radiation is placed with respect to the transparent surface such that the ultraviolet light is transmitted through the transparent surface to activate the $TiO_2$ material for facilitating removing the odor from within fresh food storage compartment 102. Additionally, the $TiO_2$ material may include sterilizing properties for facilitating preventing or reducing growth of bacteria on the surfaces and/or the food products.

In another alternative embodiment, filter medium 162 includes an adsorbent material that is positioned within an airflow path defined within fresh food storage compartment 102. It is known in the art that the airflow within fresh food storage compartment 102 follows a particular airflow path in order to effectively and consistently cool fresh food storage compartment 102. As such, the airflow path is configured to facilitate flow of air with respect to the evaporator for facilitating effectively cooling the air within fresh food storage compartment 102. In this embodiment, odor control assembly 150 is positioned within the airflow path proximate to the evaporator. The adsorbent material includes a mesh material including a suitable adsorbent material, such as activated carbon. In one embodiment, odor control assembly 150 is positioned within the cold air stream in view of the enhanced adsorptive effects at lower temperatures due to a relatively lower energy level of the odor molecules. Odor control assembly 150 is positioned with respect to the outlet of the evaporator bearing in mind that most of the odor is condensed due to the low temperature of the evaporation. This enables odor control assembly 150 to handle lower odor levels, which increases the useful life of filter medium 162. Further, in a particular embodiment defrost water from the evaporator is treated with for odor removal by passing the defrost water through activated carbon in the form of a grid or surface or a bed of granules for facilitating preventing odor being released into fresh food storage compartment 102.

In an alternative embodiment, filter medium 162 includes a condensing plate or grid that is kept at a relatively low temperature during periodic intervals and/or when a sensing mechanism senses odor within fresh food storage compartment. The condensing plate is removable for facilitating cleaning the condensing plate, as desired by the consumer and/or required for effective operation. In this embodiment, the temperature level is maintained for facilitating condensing odor across the condensing plate to de-odorize the air as the air flows across the condensing plate. In one embodiment, the existing cooling system for refrigerator 100 is used to provide the cooling effect. In an alternative embodiment, a dedicated cooling system provides the desired cooling effect.

Figure 5:
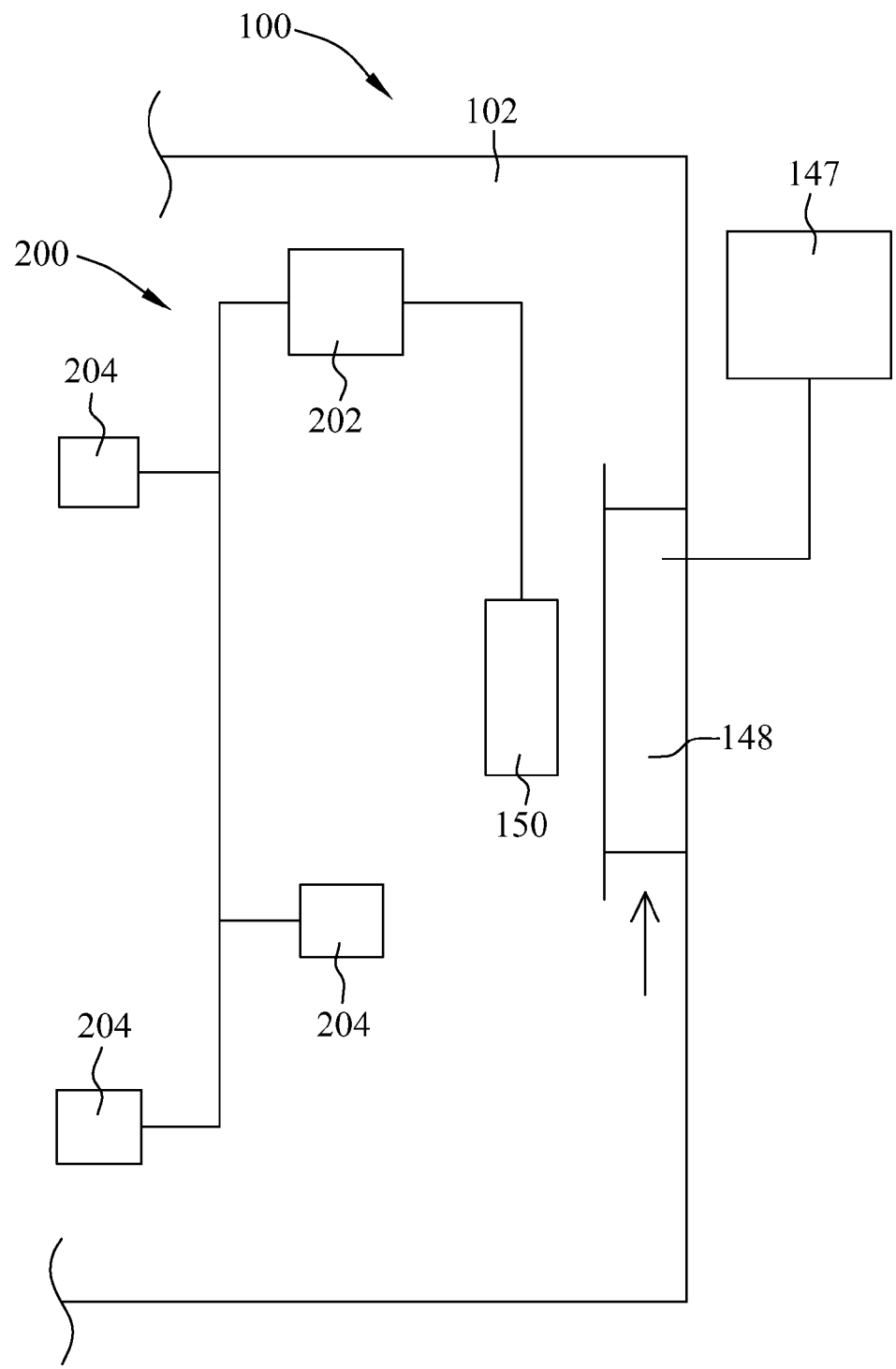
FIG. 5 is a schematic view of an exemplary odor control assembly including an odor sensing system suitable for incorporation into the refrigerator shown in FIG. 1.

FIG. 5 is a schematic view of an exemplary odor control assembly 150 suitable for incorporation into refrigerator 100 as shown in FIG. 1 for facilitating effectively monitoring and/or controlling odor within fresh food storage compartment 102. Odor control assembly 150 includes an odor sensing system 200 operatively coupled to filter medium 162. Odor sensing system 200 includes a controller 202 and at least one sensor 204 electronically coupled in signal communication with controller 202. As shown in FIG. 5, odor sensing system 200 includes a plurality of sensors 204, such as three sensors 204, positioned at selected locations within fresh food storage compartment 102 to sense or detect odor within fresh food storage compartment 102. It is apparent to those skilled in the art and guided by the teachings herein provided that any suitable number of sensors 204 may be incorporated into odor sensing system 200 for effectively and efficiently monitoring the odor level within fresh food storage compartment 102 and/or within filter medium 162. In one embodiment, odor sensing system 200 utilizes a control algorithm in cooperation with sensor 204 for facilitating active control of odor control assembly 150 to reduce odor within fresh food storage compartment 102. In this embodiment, at least one sensor 204 detects an odor within fresh food storage compartment 102 and transmits a signal to controller 202. Controller 202 utilizes the control algorithm to activate the refrigerator airflow system or fan 160 of odor control assembly 150 to force or draw air through odor control assembly 150. In one embodiment, controller 202 includes a suitable electrical circuit configured to power sensor 204 and measure an output of sensor 204.

Odor sensing system 200 provides active feedback to the consumer regarding the odor levels within refrigerator 100 and the performance of filter medium 162. In one embodiment, sensors 204 are placed at one or more selected locations within fresh food storage compartment 102 to detect and/or monitor the odor levels and provide an indication of the odor levels to the consumer. Further, sensors 204 facilitate evaluating the performance of odor control system 150 and/or filter medium 162, as well as the degradation of filter medium 162 over time, and providing feedback to the consumer for replacing the filter.

In one embodiment, sensor 204 includes a sensor element including a heated metal oxide material. The sensor element is configured to respond in the presence of odor by a reduction in resistance. Because the sensor element resistance is a function of the sensor element temperature, the sensor element resistance drifts with a change in ambient temperature. This change in the sensor element resistance due to temperature change is confounded in the presence of odor. To separate this interaction, the ambient temperature proximate sensor 204 is measured and the drift due to temperature can be calculated and removed from the total output of sensor 204.

In an alternative embodiment, because sensor 204 drifts in response to the change in ambient temperature, which leads to a change in the sensor element temperature, a power control algorithm is employed. The power control algorithm measures the ambient temperature and adjusts the power supplied to sensor 204 to maintain the element temperature constant at ambient temperatures within a desired temperature range to nullify the sensor element resistance drift due to temperature variance.

Figure 6:
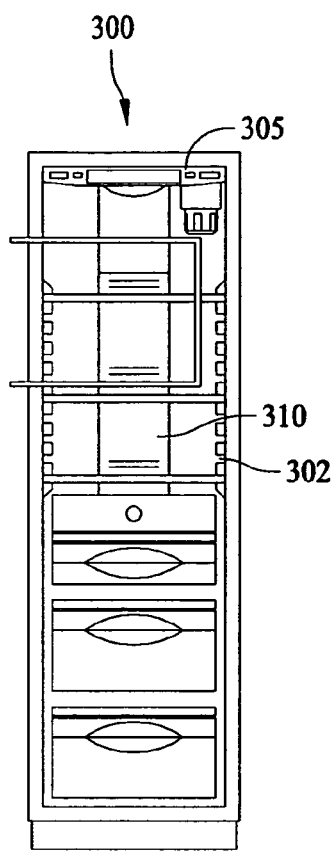
FIG. 6 is a front view of a portion of an exemplary refrigerator.
Figure 7:
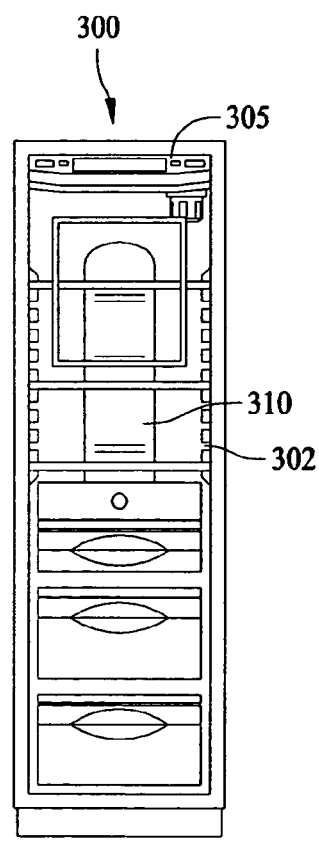
FIG. 7 is a front view of a portion of an exemplary refrigerator.

FIGS. 6 and 7 illustrate a portion of a side-by-side refrigerator 300 including a fresh food storage compartment 302. FIG. 6 illustrates fresh food storage compartment 302 provided with cooled air through a single evaporator system including one evaporator and FIG. 7 illustrates fresh food storage compartment 302 provided with cooled air through a dual evaporator system including a first independently operated evaporator positioned within fresh food storage compartment 102 and a second independently operated evaporator positioned within an adjacent freezer storage compartment (not shown). Fresh food storage compartment 302 and the freezer storage compartment are arranged side-by-side. In one embodiment, refrigerator 300 is a commercially available refrigerator from General Electric Company, Appliance Park, Louisville, Ky. 40225, and is modified to incorporate the herein described apparatus. In an alternative embodiment, refrigerator 300 is a top and bottom mount refrigerator.

A controller 305 is mounted within refrigerator 300 and is programmed to perform functions described herein. As used herein, the term "controller" is not limited to integrated circuits referred to in the art as a microprocessor, but broadly refers to computers, processors, microcontrollers, microcomputers, programmable logic controllers, application specific integrated circuits and/or other programmable circuits, and these terms are used interchangeably herein.

Refrigerator 300 includes a machinery compartment (not shown) that at least partially contains components of a vapor compression cycle system for executing a known vapor compression cycle for cooling air. The components include at least one compressor, a condenser, an expansion device, and at least one evaporator coupled in series and charged with a refrigerant. The evaporator is a type of heat exchanger that transfers heat from air passing over the evaporator to a refrigerant flowing through the evaporator, thereby causing the refrigerant to vaporize. The cooled air is used to refrigerate one or more refrigerator or freezer storage compartments via fans (not shown). Collectively, the vapor compression cycle components in a refrigeration circuit, associated fans and associated compartments are referred to herein as a "sealed system." The construction of the sealed system is well known and therefore not described in detail herein. The sealed system is operable to force cold air through the refrigerator.

As shown in FIGS. 6 and 7 an air supply duct 310 extends into fresh food storage compartment 302. Air supply duct 310 at least partially defines an airflow path 312 (shown in FIGS. 9 and 12) configured to supply cooled air to fresh food storage compartment 302. As described above, a vapor compression cycle system operates to supply cooled air through airflow path 312 into fresh food storage compartment 302. In this embodiment, the vapor compression cycle system includes at least one evaporator. The vapor compression cycle system is charged with a refrigerant and configured to transfer heat from the air within airflow path 312 to the refrigerant as the air passes over the evaporator.

Figure 8:
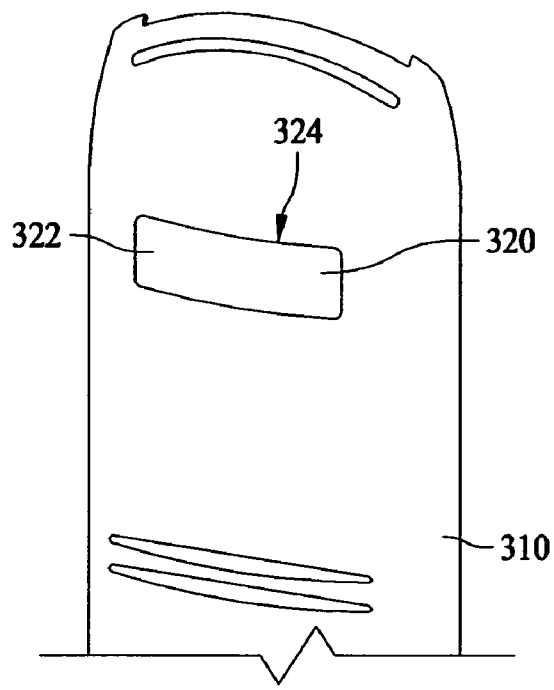
FIG. 8 is a perspective front view of a portion of an air supply duct suitable for incorporation into the refrigerator shown in FIG. 7.
Figure 9:
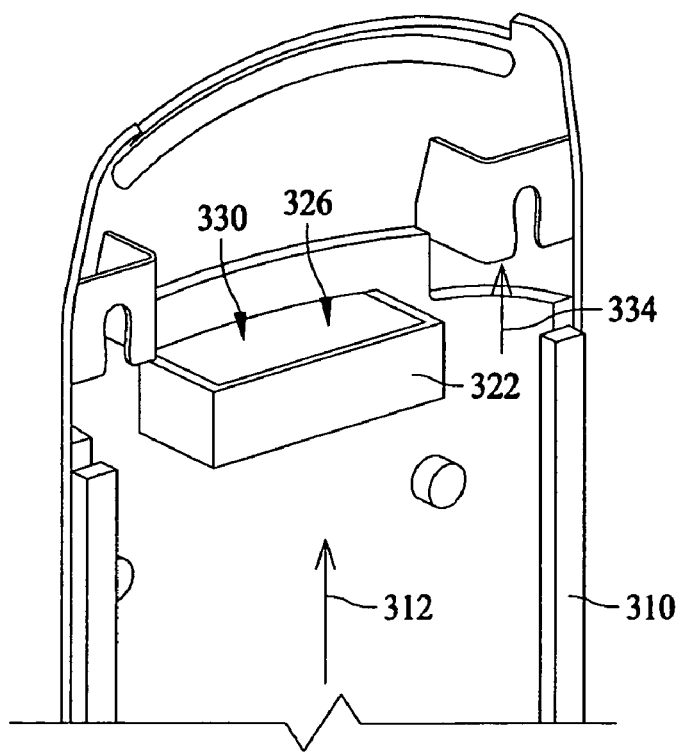
FIG. 9 is a perspective back view of the portion of the air supply duct shown in FIG. 8.
Figure 10:
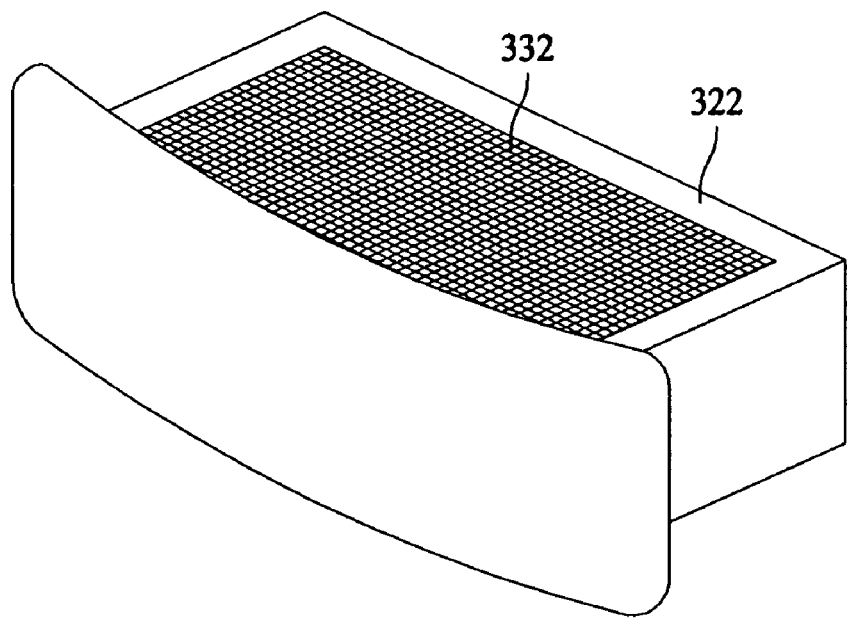
FIG. 10 is a perspective view of an exemplary odor control assembly.

Referring further to FIGS. 8-10, refrigerator 300 includes an odor control assembly 320 for controlling and/or removing odor within refrigerator 300. Odor control assembly 320 is mounted at a suitable location within fresh food storage compartment 302 and configured to regulate and/or control a level of odor emitted from the food products stored within fresh food storage compartment 302. In alternative embodiments, odor control assembly 320 is mounted with respect to any suitable location within the adjacent freezer storage compartment. In one embodiment, odor control assembly 320 is a dedicated system that operates independently from the refrigerator control system for facilitating efficient and effective odor control and design flexibility.

Odor control assembly 320 includes a frame 322 that is removably positioned within an airflow path configured to supply cooled air to fresh food storage compartment 302. In one embodiment, frame 322 is removably positioned within an opening 324 defined within air supply duct 310. In a particular embodiment, frame 322 includes at least one indentation and/or projection, such as a finger grip or handle, for facilitating removing frame 322 from within air supply duct 310. Frame 322 defines a chamber 326 extending into at least a portion of airflow path 312, as shown in FIG. 9. A suitable filter medium 330 is positioned within frame 322. Filter medium 330 is configured to filter air channeled therethrough and remove odorous molecules. As shown in FIG. 10, frame 322 defines a plurality of openings 332 for facilitating channeling air through filter medium 320. In one embodiment, filter medium 330 is permanently or integrally contained within chamber 326. In a particular embodiment, filter medium 330 is integrally molded, formed or inserted into frame 322. In this embodiment, odor control assembly 320, including filter medium 330, is removable from within air supply duct 310 and disposable. A replacement odor control assembly 320 is then positioned within opening 324 and coupled to air supply duct 310.

As shown in FIG. 9, frame 322 extends partially into airflow path 312 to filter a portion of the cooled air supplied through airflow path 312. Frame 322 is positioned within opening 324 such that chamber 326 extends partially into airflow path 312 defined within air supply duct 310. With chamber 326 partially extending into airflow path 312, frame 322 at least partially defines a by-pass path 334 within airflow path 312. In one embodiment, by-pass path 334 is defined between frame 322 and an interior liner of fresh food compartment 302. By-pass path 334 is configured to provide a secondary airflow path should filter medium 330 become clogged and/or inoperable preventing airflow therethrough and/or obstructing airflow path 312. In one embodiment, by-pass path 334 is defined within about 50% of a cross-sectional area of airflow path 312. In alternative embodiments, by-pass path 334 defines less than about 50% of the cross-sectional area of airflow path 312 or greater that about 50% of the cross-sectional area of airflow path 312.

Figure 11:
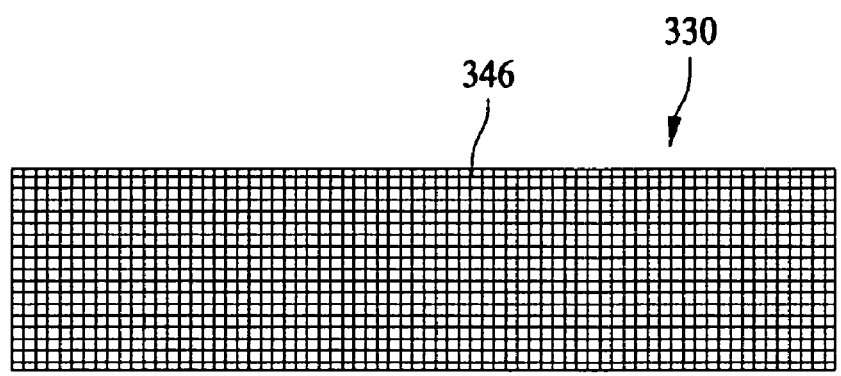
FIG. 11 is a top view of a filter medium of the odor control assembly shown in FIG. 10.

Referring to FIG. 11, in one embodiment filter medium 330 is formed as a honeycomb structure 340 having a suitable porosity for providing surface area. In this embodiment, filter medium 330 includes an activated carbon material. In a further embodiment, filter medium 330 includes a catalyst dispersed within honeycomb structure 340 and/or applied to at least a portion of a surface of honeycomb structure 340. In this embodiment, the catalyst material contacts the odor molecules held within and/or passing through filter medium 320. The catalyst material facilitates a reaction between the odor molecules and the surrounding air and/or moisture to create by-products that are generally non-odorous. In a particular embodiment, filter medium 320 includes an activated carbon material with a low temperature catalyst, such as manganese dioxide ($MnO_2$), dispersed within filter medium 330 or applied to at least a portion of a surface of filter medium 330 to improve the useful life of filter medium 330 by replenishing the activated carbon. It is apparent to those skilled in the art and guided by the teachings herein provided that other suitable materials may be used to make filter medium 330. In an alternative embodiment, filter medium 330 includes a plurality of granules contained within a porous fabric material.

In a further alternative embodiment, filter medium 330 includes a photocatalyst material, such as titanium dioxide ($TiO_2$) that is coated on a surface of filter medium 330, on a surface of air supply duct 320 and/or other surfaces within fresh food storage compartment 302. In this alternative embodiment, the coated surfaces are irradiated with an ultraviolet light having a wavelength of about 360 nm. The photocatalyst is energized with the ultraviolet light for facilitating a reaction between the odor molecules, oxygen and/or moisture in the surrounding air. In a particular embodiment, surfaces within fresh food storage compartment 102 which contact odorous food products are coated with the filtering material. Transparent surfaces, such as surfaces of shelves and/or pans placed within fresh food storage compartment, are coated with a $TiO_2$ material. The ultraviolet light radiation is placed with respect to the transparent surface such that the ultraviolet light is transmitted through the transparent surface to activate the $TiO_2$ material for facilitating removing the odor from within fresh food storage compartment 302. Additionally, the $TiO_2$ material may include sterilizing properties for facilitating preventing or reducing growth of bacteria on the surfaces and/or the food products.

Figure 12:
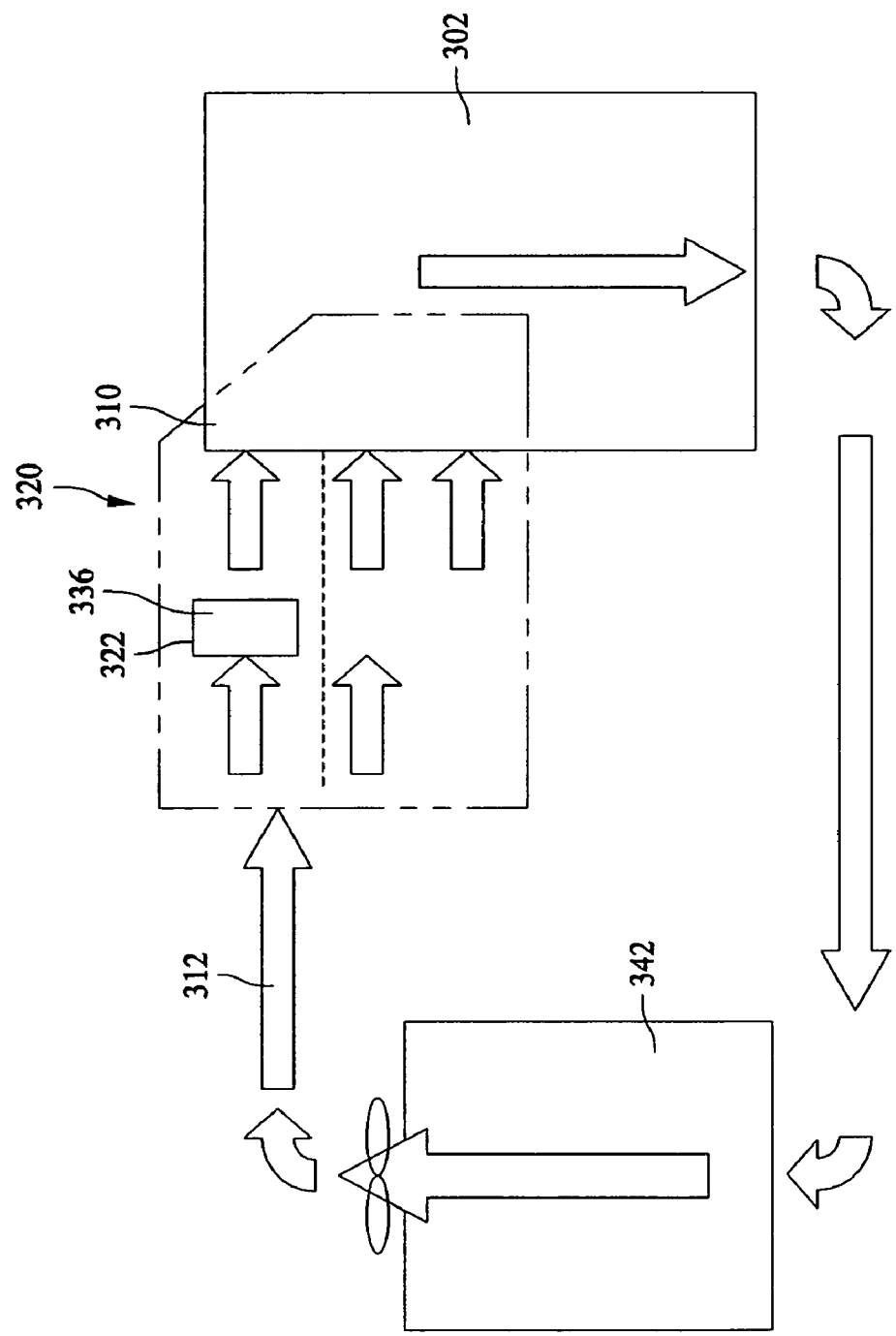
FIG. 12 is a schematic view of an exemplary odor control assembly positioned within an airflow path defined within the refrigerator shown in FIG. 7.

In one embodiment, a method is provided for removing an odor from within fresh food storage compartment 302 or any suitable food storage compartment. Referring to FIG. 12, odor control assembly 320 is positioned with respect to airflow path 312 at least partially defined within air supply duct 310. Airflow path 312 is configured to supply cooled air to fresh food storage compartment 302. In a particular embodiment, odor control assembly 320 includes frame 322 removably positioned within airflow path 312. Frame 322 defines chamber 326 within which filter medium 330 is positioned. Filter medium 330 is configured to filter air channeled therethrough and remove odorous molecules.

A vapor compression cycle system operates to supply cooled air through air supply duct 310 into fresh food storage compartment 302. In this embodiment, the vapor compression cycle system includes at least one evaporator 342. The vapor compression cycle system is charged with a refrigerant and configured to transfer heat from the air within airflow path 312 to the refrigerant as the air passes over evaporator 342. At least a portion of the cooled air is channeled through odor control assembly 320 for facilitating removing odorous molecules from the channeled air.

Referring to FIGS. 8-10, in one embodiment, frame 322 is removably positioned within opening 324 defined in air supply duct 320. Air supply duct 320 at least partially defines airflow path 312. Frame 322 extends partially into airflow path 312 to filter a portion of the cooled air supplied through the airflow path. With frame 322 removably positioned within air supply duct 320, frame 322 at least partially defines by-pass path 334 within airflow path 312 By-pass path 334 is configured for facilitating preventing obstruction of airflow path 312 should filter medium 330 become clogged and/or inoperable.

The above-described apparatus and method for controlling odors within an appliance, such as a refrigerator, facilitates reducing the odor level to a significantly lower level as perceived by a human's sense of smell in an effective and efficient manner. More specifically, the apparatus and method facilitate reducing odor within a refrigerator storage compartment, wherein an odor level is sensed to enable active control of the odor level and provide feedback to the consumer. As a result, the odor level within the refrigeration storage compartment is effectively and efficiently lowered as perceived by the consumer's sense of smell.

Exemplary embodiments of an apparatus and method for controlling odors within an appliance, such as a refrigerator, are described above in detail. The apparatus and method is not limited to the specific embodiments described herein, but rather, components of the apparatus and/or steps of the method may be utilized independently and separately from other components and/or steps described herein. Further, the described apparatus components and/or method steps can also be defined in, or used in combination with, other apparatus and/or methods, and are not limited to practice with only the apparatus and method as described herein.

While the invention has been described in terms of various specific embodiments, those skilled in the art will recognize that the invention can be practiced with modification within the spirit and scope of the claims.

What is claimed is:

1. An apparatus for controlling odor within a refrigeration appliance that includes an airflow system for channeling cooled air through an airflow path and an evaporator for cooling air within the airflow path, said apparatus comprising:

a frame positioned within a food storage compartment of the refrigerator, the frame comprising an inner surface extending between a first open end and a second open end opposite said first open end, said inner surface defining a chamber extending between said first open end and said second open end, said frame removably positioned proximate to an outlet of the evaporator such that the cooled air is at least partially channeled from the evaporator through said frame from said first end to said second end to facilitate removing odor from the cooled air;

a filter medium positioned within said chamber such that said inner surface circumscribes said filter medium, said filter medium configured to filter air channeled therethrough and remove odorous molecules; and an odor sensing system operatively coupled to the refrigeration appliance for facilitating activating the airflow system to channel air through said filter medium upon sensing an odor, said odor sensing system comprising:

a first sensor positioned within the food storage compartment, said first sensor configured to sense an odor within the food storage compartment and to transmit a first signal indicative of the sensed odor, said first sensor having an electrical resistance that is configured to be reduced upon exposure to an odor;

a second sensor positioned within the food storage compartment, said second sensor configured to sense a temperature within the food storage compartment and transmit a signal indicative of the sensed temperature; and a controller coupled to said first and second sensors and configured to channel air through the filter medium upon said first sensor sensing an odor within the food storage compartment, said controller further configured to adjust a power supplied to said first sensor based at least in part on the sensed temperature to facilitate adjusting the electrical resistance of said first sensor.

2. An apparatus in accordance with claim 1 wherein the refrigerator appliance includes an air supply duct that at least partially defines the airflow path, said frame is removably inserted through an opening formed in the air supply duct.

3. An apparatus in accordance with claim 2 wherein said frame extends partially into the airflow path to filter a portion of the cooled air supplied through the airflow path.

4. An apparatus in accordance with claim 3 wherein said frame at least partially defines a by-pass path within the airflow path, said by-pass path configured for facilitating preventing obstruction of the airflow path.

5. An apparatus in accordance with claim 1 wherein said frame defines a plurality of openings for facilitating channeling air through said filter medium.

6. An apparatus in accordance with claim 1 wherein said filter medium is integrally contained within said chamber.

7. An apparatus in accordance with claim 1 wherein said filter medium comprises a honeycomb structure comprising activated carbon.

8. An apparatus in accordance with claim 7 wherein said filter medium further comprises a catalyst dispersed within said honeycomb structure.

9. An apparatus in accordance with claim 8 wherein said catalyst comprises $MnO_2$.

10. An apparatus in accordance with claim 1 wherein said filter medium comprises a plurality of granules contained within a porous material.

11. An apparatus in accordance with claim 1 wherein said frame is coupled to an interior liner of the refrigeration appliance.

12. An apparatus in accordance with claim 11 further comprising a fan coupled to said first end, said fan configured for facilitating channeling air through said chamber.

13. An apparatus in accordance with claim 12 further comprising:

a grill positioned over said fan and coupled to said first end such that said fan is positioned between said first end and said grill; and a cap rotatably coupled to said second end, said cap comprising an inner surface defining a cavity sized to receive said filter medium therein such that said cap inner surface circumscribes said filter.

14. An apparatus in accordance with claim 12, wherein said odor sensing system is operatively coupled to said fan for operating said fan upon sensing an odor.

15. An apparatus in accordance with claim 1 wherein said first sensor is further configured to sense an odor within said filter medium and to transmit a signal indicative of the sensed filter medium odor to said controller, said controller is configured to determine a performance of said filter medium based on the sensed filter medium odor.

16. An apparatus in accordance with claim 1 wherein said first sensor comprises a metal oxide material.

17. An apparatus in accordance with claim 1 wherein said controller is configured to calculate an odor level within the food storage compartment based on the received first signal, and indicate the calculated odor level to a user.

\* \* \* \* \*